US012653967B2

(12) United States Patent　　　　　(10) Patent No.:　US 12,653,967 B2
Noh　　　　　　　　　　　　　　　　　(45) Date of Patent:　　　Jun. 16, 2026

(54) NEEDLE CARTRIDGE FOR DRUG INJECTION AND DRUG INJECTION DEVICE INCLUDING THE SAME

(71) Applicants:NOBAMEDI CO., LTD., Yongin-si (KR); Hyun Mee Noh, Yongin-si (KR)

(72) Inventor:　Hyun Mee Noh, Yongin-si (KR)

(73) Assignees: NOBAMEDI CO., LTD., Yongin-si (KR); Hyun Mee Noh, Yongin-si (KR)

( * ) Notice:　Subject to any disclaimer, the term of this patent is extended or adjusted under 35 U.S.C. 154(b) by 462 days.

(21) Appl. No.: 18/502,924

(22) Filed:　　Nov. 6, 2023

(65)　　　　　Prior Publication Data

US 2025/0144322 A1　　May 8, 2025

(51) Int. Cl.
　　　*F04D 25/08*　　　(2006.01)
　　　*A61M 5/31*　　　(2006.01)
　　　*A61M 5/34*　　　(2006.01)
　　　*A61M 5/46*　　　(2006.01)
　　　*F04D 29/52*　　　(2006.01)
　　　*F04D 29/54*　　　(2006.01)
　　　*F04D 29/66*　　　(2006.01)
　　　*A61M 37/00*　　　(2006.01)
(52) U.S. Cl.
　　　CPC ............ *A61M 5/46* (2013.01); *A61M 5/3148* (2013.01); *A61M 5/344* (2013.01); *A61M 37/0076* (2013.01)

(58) Field of Classification Search
　　　CPC ...... A61M 5/3148; A61M 5/344; A61M 5/46; A61M 2037/0023; A61M 2037/003; A61M 37/0076; A61M 37/0084
　　　See application file for complete search history.

(56)　　　　　References Cited

U.S. PATENT DOCUMENTS

2020/0121769 A1 *　4/2020　Chang ............... A61M 37/0015
2021/0244496 A1 *　8/2021　Niven .................... A61B 90/39

FOREIGN PATENT DOCUMENTS

KR　　　2020100008769 U　　9/2010
KR　　　　　101380189 B1　　4/2014

* cited by examiner

*Primary Examiner* — Wesley G Harris
*Assistant Examiner* — Charles W Nichols
(74) *Attorney, Agent, or Firm* — Rabin & Berdo, P.C.

(57)　　　　　ABSTRACT

A needle cartridge for drug injection and a drug injecting device including the same are provided. The needle cartridge includes a needle, a handpiece body including a syringe formed on an upper portion, and a cartridge coupling unit and a needle coupling unit formed on a front, a syringe pressing unit including a power source, a shaft connected to the power source and rotated, and a pusher which is coupled to the shaft, is inserted into a moving groove formed in the upper portion of the handpiece body, and is moved to push a plunger of the syringe, a needle driving unit mounted inside the handpiece body and reciprocating the needle in forward and backward directions, and a position control unit that moves a position of the needle driving unit within the handpiece body to adjust a length of a needle drawn out of the needle cartridge.

6 Claims, 8 Drawing Sheets

(a)

(b)

NEEDLE CARTRIDGE FOR DRUG INJECTION AND DRUG INJECTION DEVICE INCLUDING THE SAME

BACKGROUND

Field

The present disclosure relates to a needle cartridge for drug injection and a drug injection device containing the same, and more specifically, to a needle cartridge for drug injection, which is used in various cosmetic skin procedures including skin care, skin treatment, or tattooing, which can be stably filled with a chemical solution, and in which a needle is applied with the chemical solution on a surface thereof as the needle is passed through the chemical solution, so that when the needle is penetrated through the skin, the chemical solution can be injected into the skin at the same time as the puncture occurs, thus enabling to inject the drug into the skin quickly and accurately.

Description of Related Art

In general, cosmetic skin procedure is performed using various treatment methods for various purposes such as cosmetic treatment, skin treatment, or tattooing, and also performed for various other surgical needs.

The cosmetic skin procedure for the purpose of cosmetic or skin treatment, including removal of wrinkles, acne, dead skin cells, and so on, is performed by creating hundreds to tens of thousands of microscopic punctures in the human skin using needles so as to allow new skin to grow with the self-regenerative power of skin tissue damaged during this process, and by applying a therapeutic drug to the area where the microscopic punctures are formed so that the drug penetrates into the skin through the microscopic punctures, thereby maximizing the effect of the treatment.

In addition, for the cosmetic skin procedure for tattooing, in the process of piercing the skin to a certain depth using a needle, the tattoo ink penetrates through the needle and into the skin, so that a predetermined pattern is expressed on the human skin as intended by the practitioner.

The cosmetic skin procedure device used for such cosmetic skin procedure includes a needle unit for use with the cosmetic skin procedure device, which includes needles provided at a front end, and a needle slider movably provided at a rear end and connected to a drive axis of the cosmetic skin procedure device reciprocating linearly in the forward and backward directions.

Korean Utility Model Registration No. 20-0458906 discloses a needle unit for tattooing, which can be driven forward and backward by the driving unit of the tattoo device.

In the related art, the needle unit for tattooing is disclosed, which includes a connecting member connected to one side of the driving unit, a plurality of needles, with one side thereof being seated on a part of the connecting member and arranged in close contact in succession on the same plane, and a fixing cover for fixing one side of the plurality of needles to the connecting member.

The related art suggests that the drug or ink is applied on and absorbed into the skin as the needle pierces the skin, but when the related art is actually used, there is a problem that the body fluid is discharged upon the needle piercing the skin, making the drug or ink, which is supplied later, stay only on the skin surface so that the amount of drug or ink actually injected into the surface area is a far less than desired and the treatment effect is minimal.

Meanwhile, the related art has a disadvantage of not being able to finely control the depth of insertion of the needle.

In addition, although the related art proposes that the drug or ink is applied to and absorbed into the skin after the needle pierces the skin, when the related is actually used, there is a problem that the body fluid is discharged first as the needle pierces the skin, making the drug or ink, which is supplied later, stay only on the skin surface so that the amount drug or ink actually injected into the surface area is very small and the treatment effect is minimal.

SUMMARY

The present disclosure was created to solve the problems of the related art, and an object of the present disclosure is to provide a needle cartridge that can be filled with and maintain a certain amount of chemical solution inside, and in which the needle with the filled chemical solution applied thereon punctures the skin, thereby enabling injection of the chemical solution at the same time as the puncture, thereby improving the injection efficiency of the chemical solution.

An object of the present disclosure is to provide a drug injection device for cosmetic skin procedure, in which needles are applied, on the surfaces thereof, with chemical solution including drug, pigments, and ink filled in the needle cartridge and then inserted into the skin so that it is possible to inject the chemical solution into the skin concurrently as the needles applied with the chemical solution pierce the skin leaving punctures, such that the injection efficiency of the chemical solution can be improved, and the length by which the needles are pulled out can be finely adjusted, thereby improving the accuracy of the procedure.

Solution to Problem

In order to achieve the above and other objects, a needle cartridge for drug injection and a drug injecting device including the same are provided, which may include the needle cartridge including a needle, a handpiece body including a syringe formed on an upper portion, and a cartridge coupling unit and a needle coupling unit formed on a front, a syringe pressing unit including a power source mounted inside the handpiece body, a shaft connected to the power source and rotated, and a pusher which is coupled to the shaft, is inserted into a moving groove formed in a longitudinal direction in the upper portion of the handpiece body, and is moved to push a plunger of the syringe, a needle driving unit mounted inside the handpiece body and reciprocating the needle of the needle cartridge in forward and backward directions, and a position control unit that moves a position of the needle driving unit in the handpiece body to adjust a length of the needle pulled out of the needle cartridge.

The needle cartridge may include a cartridge body to be in contact with skin, a needle assembly coupled within the cartridge body, and a fitting tube body coupled to a rear end of the cartridge body and having an injection port formed on an outer peripheral surface, the cartridge body may include an opening formed at one end to be in contact with the skin, a connection end formed at other end and coupled with the fitting tube body, and a partition wall formed within the cartridge body and connected to the injection port, a flow path is formed between the partition wall and an inner peripheral surface of the cartridge body, the needle assembly may include the rod to be inserted into the fitting tube body and coupled with the needle driving unit, the fitting tube body may include an opening formed on one side and into which the connection end is fitted, and a mounting end formed on the outer peripheral surface on other side, and the mounting end is coupled with the handpiece body and fixed so as not to be moved, in which an end of the partition wall is spaced apart from the opening, defining a space therebetween, and when the cartridge body is brought into contact with the skin, the space is filled with a chemical solution.

The needle assembly may include the rod to be inserted into the fitting tube body and coupled with the needle driving unit, the fitting tube body may include an opening formed on one side and into which the connection end is fitted, and a mounting end formed on the outer peripheral surface on other side, and the mounting end may include a protrusion formed thereon, the needle coupling unit may include a bar having a predetermined length, a ring part formed at one end of the bar and having a coupling hole coupled with a bearing, and a fastening tube body formed at the other end of the bar and having a protrusion coupling hole into which the rod of the needle cartridge is coupled, the needle assembly may include the rod to be inserted into the fitting tube body and coupled with the needle driving unit, the cartridge coupling unit may be open on both ends, and may include a passage formed therein, and an insertion groove formed on an outer peripheral surface, and the protrusion of the mounting end and the insertion groove of the cartridge coupling unit may be fitted with each other.

The needle driving unit may include a first motor disposed with an axis facing upward, a motor mounting case to which the axis is coupled, on which the first motor is mounted, and which is connected to the needle coupling unit, a bearing inserted into the motor mounting case and eccentrically coupled with the axis, and a cap coupled to the top of the shaft.

A guiding means for guiding forward and backward movement of the motor mounting case may be included, in which the guidance means may include a guide piece protruding from a side of a motor mounting case, and a guide rail unit formed on the inner peripheral surface of the handpiece body and coupled with the guide piece, the motor mounting case may include an opening formed on one side, the needle coupling unit may include a ring part having a coupling hole coupled to a bearing of the needle driving unit, and the ring part may be inserted into the opening and fitted with the bearing.

The power source may be a second motor with an axis disposed horizontally, in which the shaft may be connected to the axis of the second motor and disposed horizontally, and a body formed on a lower portion of the pusher may be coupled to the shaft.

The position control unit may include an operating axis coupled to a motor mounting case of the needle driving unit and including threads formed on a portion thereof, and a handle coupled to the other end of the operating shaft and formed on an outside of a handpiece body.

According to the present disclosure, the needle cartridge can be stably filled with a chemical solution including drug, pigment or ink so as to inject the same into the skin, and configured such that a needle is applied with the chemical solution on a surface thereof as the needle is passed through the chemical solution, thus allowing the chemical solution to be injected into the skin at the same time as the needle punctures the skin, thus providing the effect of improving the injection efficiency of the chemical solution.

According to the present disclosure, it is possible to finely adjust the length by which the needles are pulled out, and thus improve the accuracy of the procedure.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION

Figure 1:
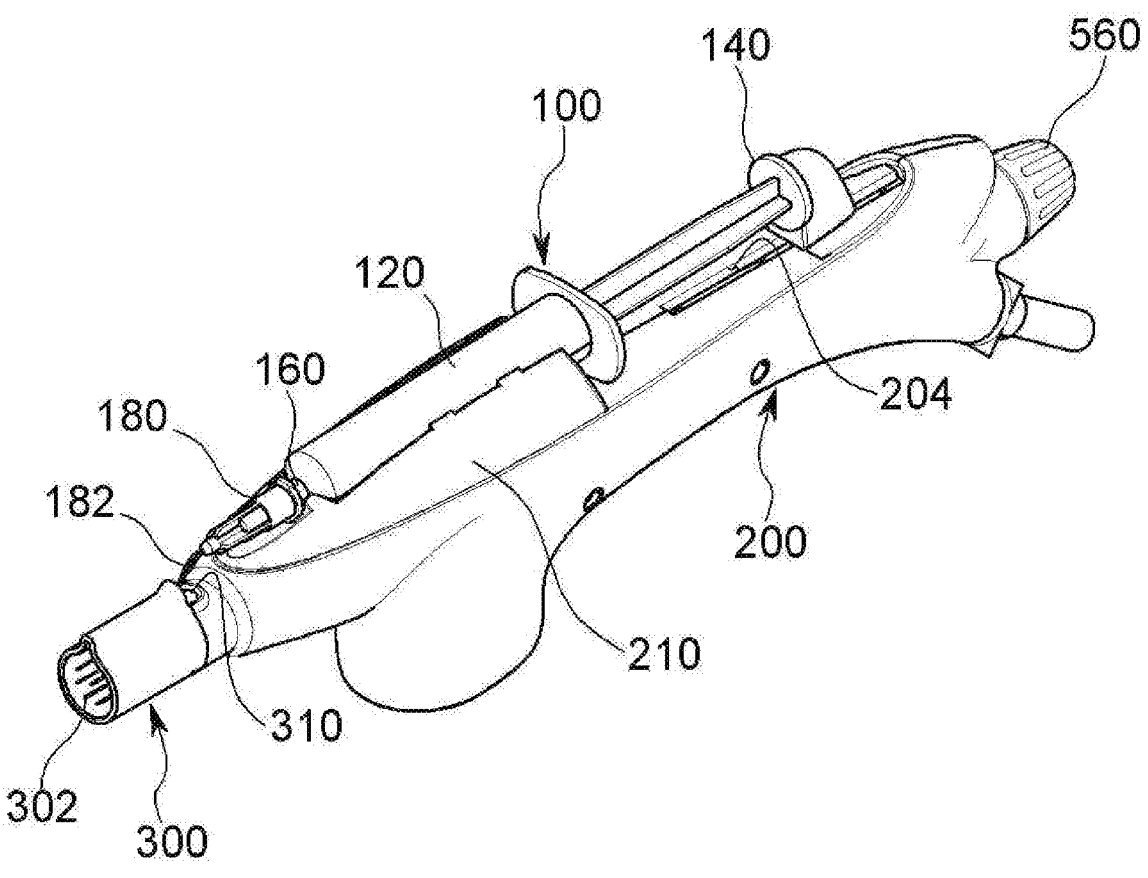
FIG. 1 is a perspective view of a needle cartridge for drug injection and a drug injection device including the same.

Hereinafter, the preferred embodiment will be described in detail below based on the attached drawings.

The examples to be described below are intended to explain the present disclosure in detail such that a person skilled in the art can easily practice the present disclosure, and do not mean that the technical idea and scope of the disclosure are limited.

In addition, it is to be noted that the size or shape of the components shown in the drawings may be exaggerated for clarity and convenience of explanation, and terms specifically defined in consideration of the configuration and operation of the present disclosure may vary according to the intention or custom of the user or operator, and these terms should be defined based on the content throughout this specification.

Figure 2:
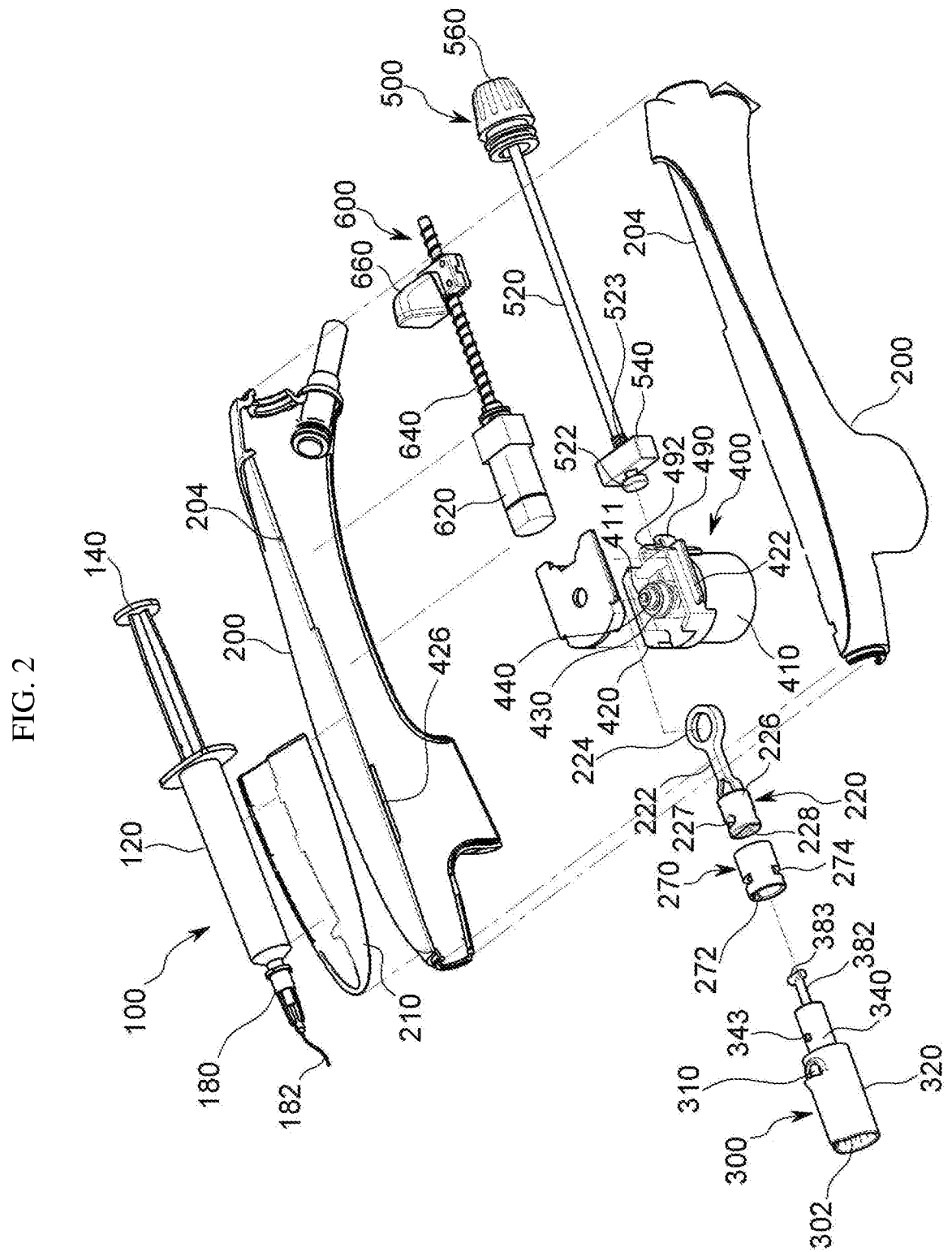
FIG. 2 is an exploded perspective view of the needle cartridge for drug injection and the drug injection device including the same.
Figure 3:
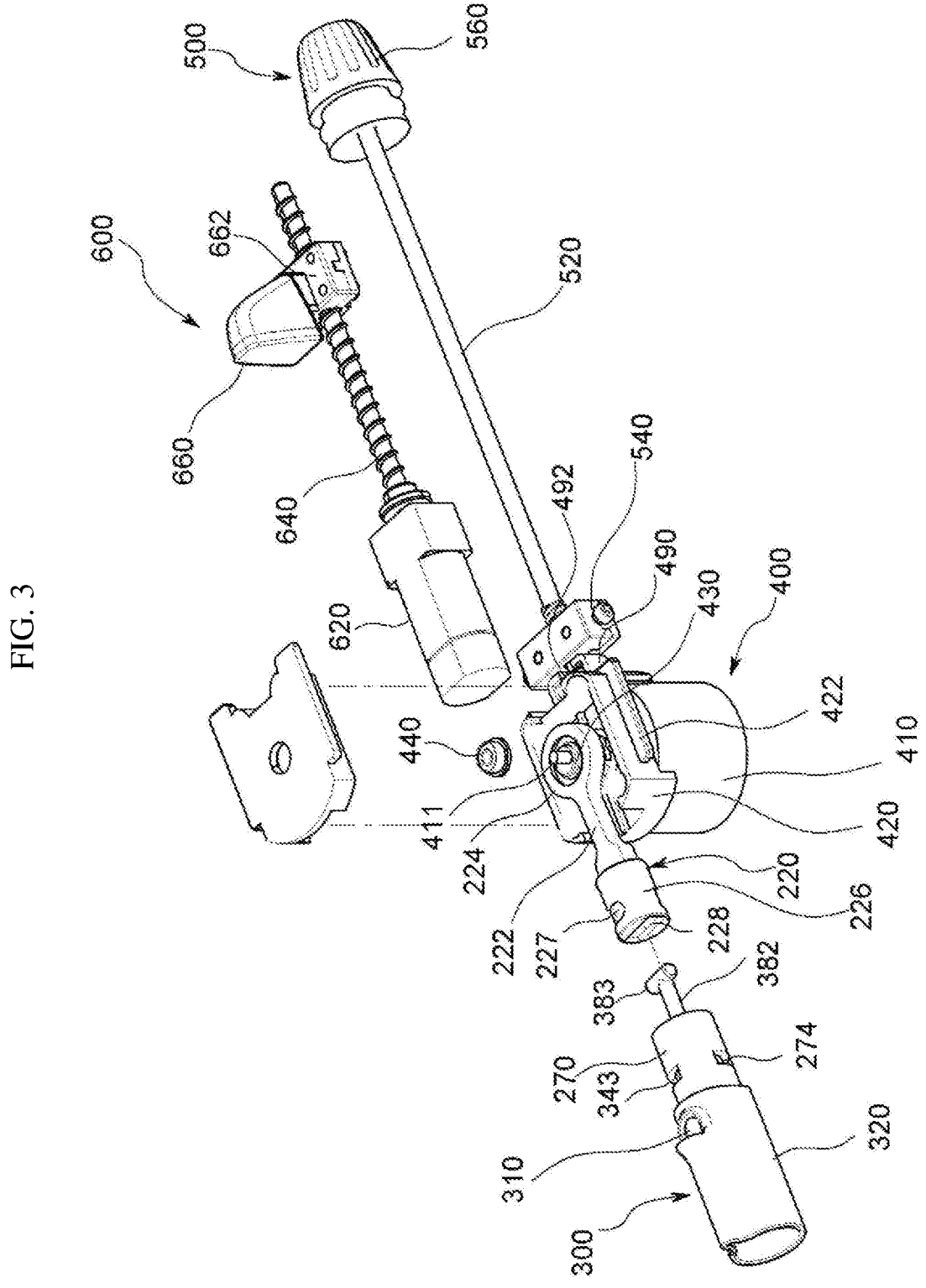
FIG. 3 is an exploded perspective view illustrating in part the needle cartridge for drug injection and the drug injection device including the same.
Figure 4:
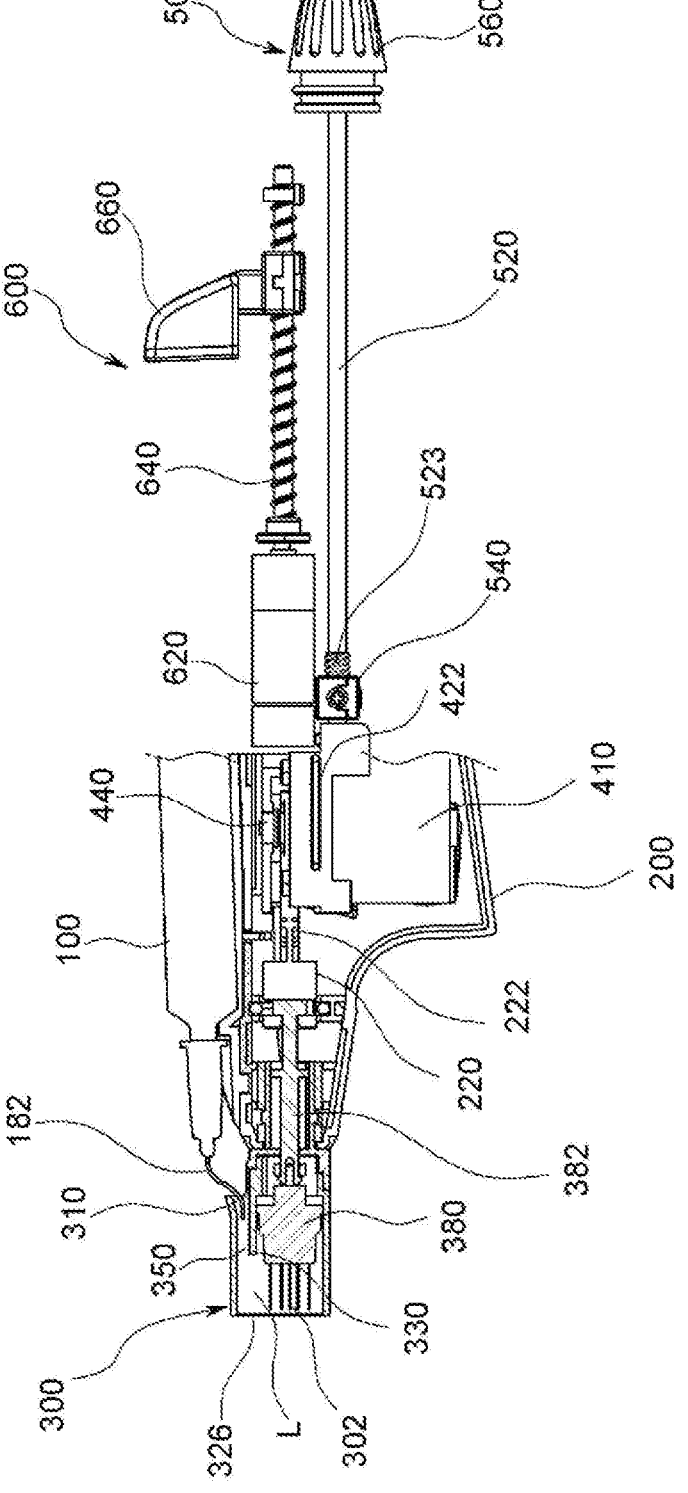
FIG. 4 is cross-sectional view of the needle cartridge for drug injection and the drug injection device including the same.
Figure 5:
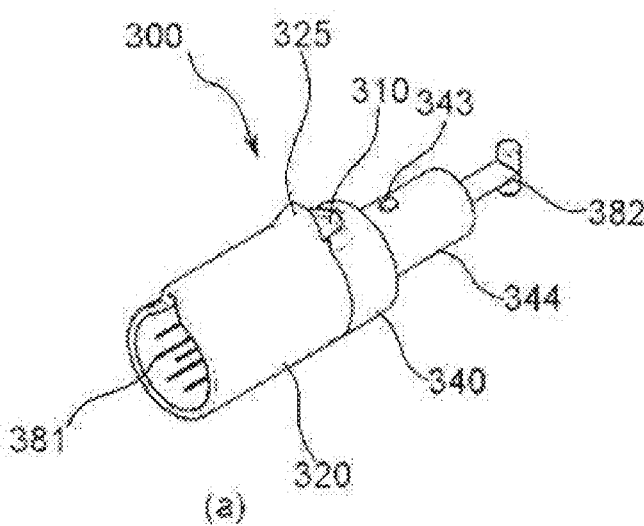
FIG. 5 is a perspective view of the needle cartridge.
Figure 5:
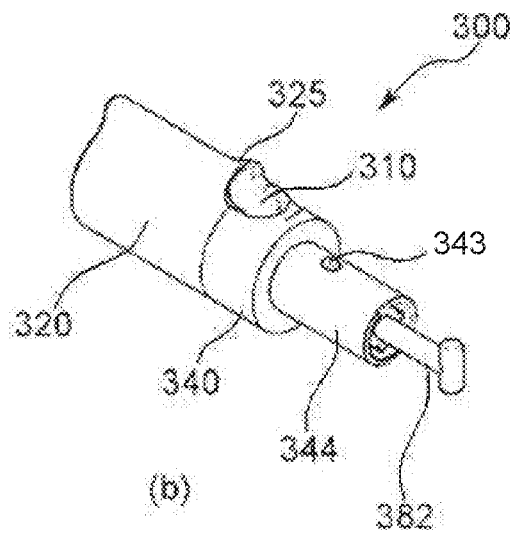
Figure 6:
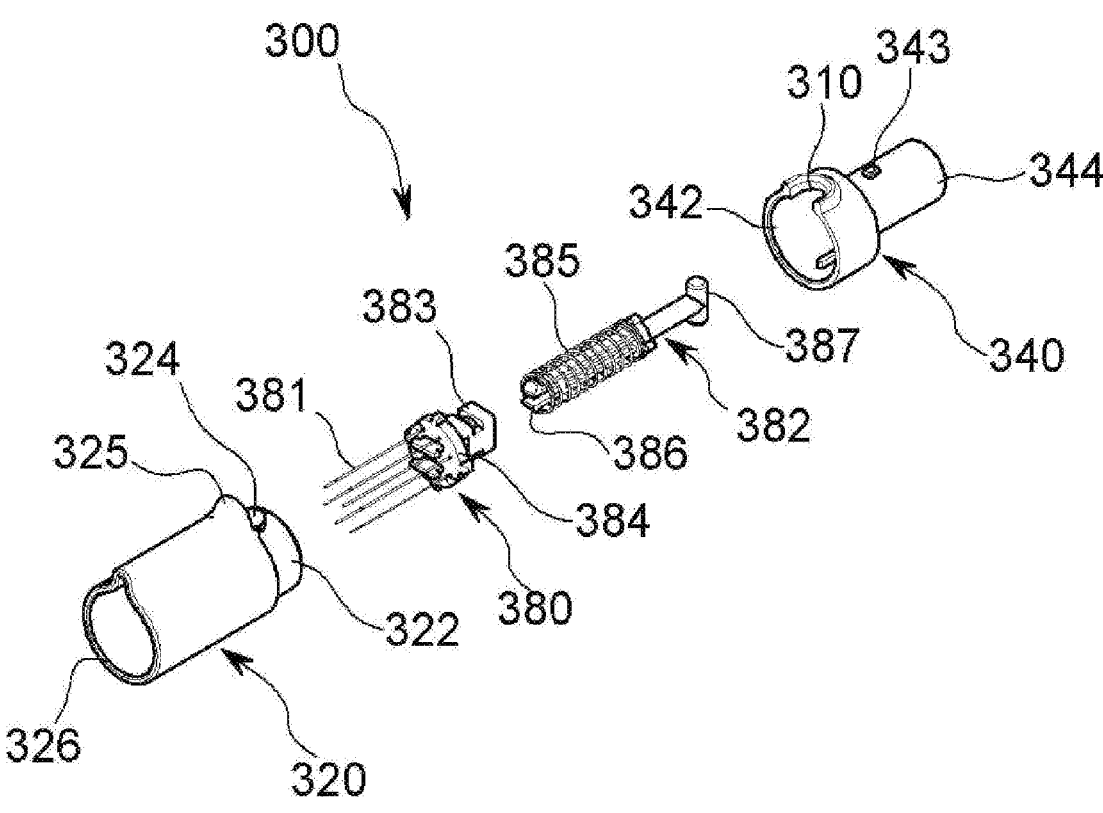
FIG. 6 is an exploded perspective view of the needle cartridge.
Figure 7:
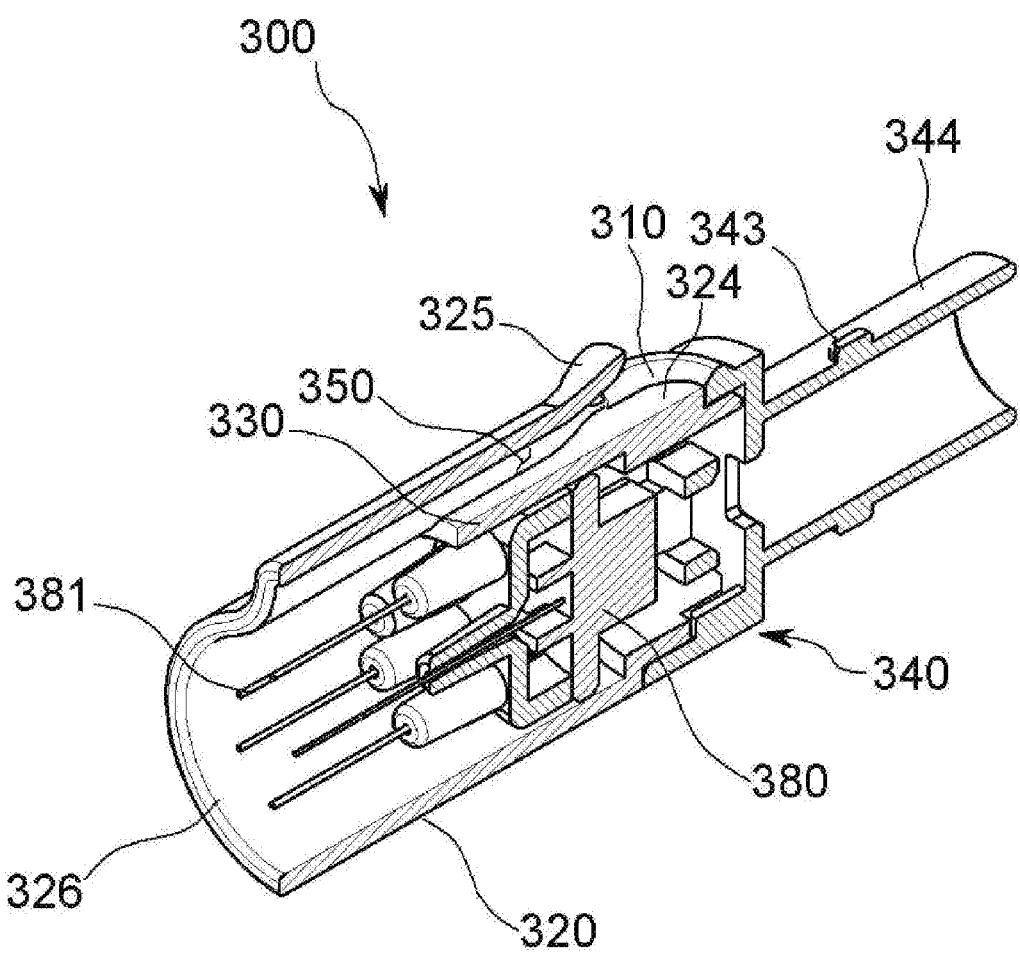
FIG. 7 is a cross-sectional perspective view of the needle cartridge.
Figure 8:
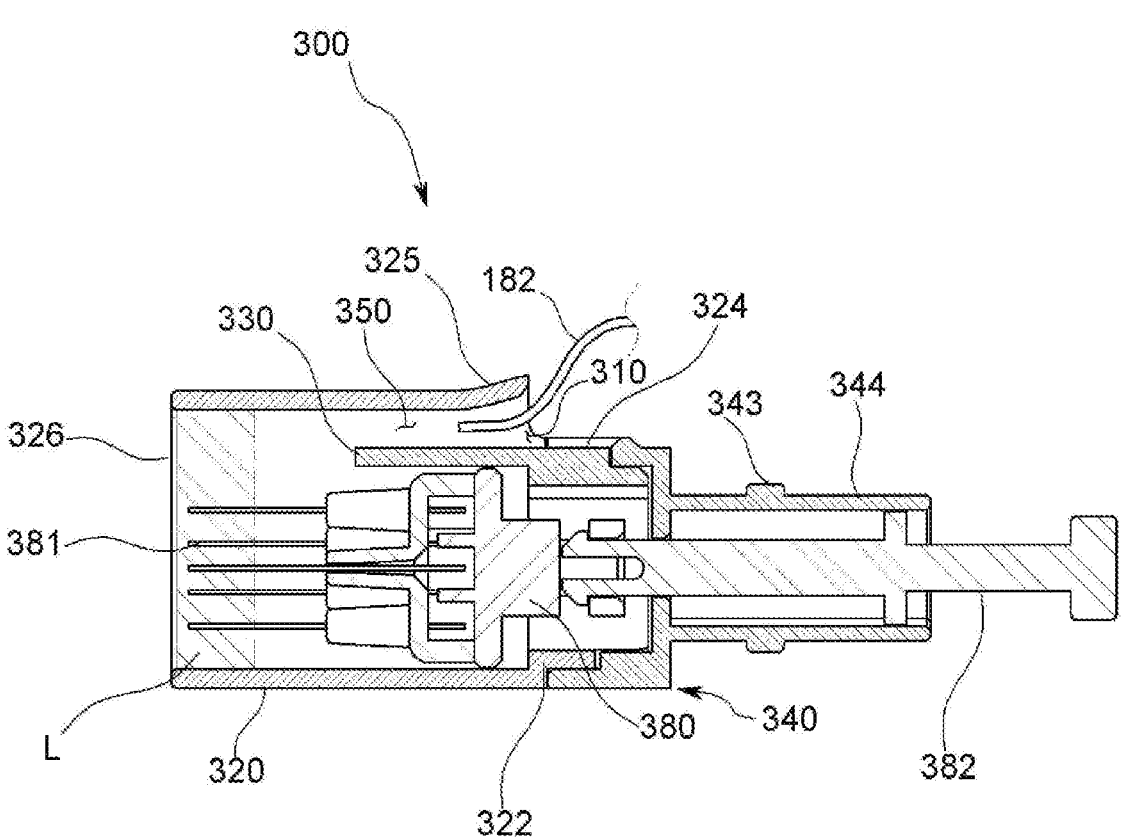
FIG. 8 is a front cross-sectional view of the needle cartridge.

In the accompanying drawings, FIG. 1 is a perspective view of a needle cartridge for drug injection and a drug injection device including the same, FIG. 2 is an exploded perspective view, FIG. 3 is an exploded perspective view illustrating the same in part, FIG. 4 is cross-sectional view, FIG. 5 is a perspective view of the needle cartridge, FIG. 6 is an exploded perspective view of the needle cartridge, FIG. 7 is a cross-sectional perspective view of the needle cartridge, and FIG. 8 is a front cross-sectional view of the needle cartridge.

As shown in FIGS. 1 to 8, a needle cartridge for drug injection and a drug injection device including the same includes a syringe 100, a needle cartridge 300, a handpiece body 200, a syringe pressing unit 600, a needle driving unit 400, and a position control unit 500.

The syringe 100 includes a barrel 120 containing chemical solution, a plunger 140 coupled in the barrel 120 and injecting the chemical solution, a tip 160 which is formed at a front of the barrel 120 and through which the chemical solution is discharged, a cover 180 coupled to the tip 160, and an injection needle 182 connected to the cover 180.

The needle cartridge 300 includes a cartridge body 320 to be in contact with the skin, a needle assembly 380 coupled within the cartridge body 320, and a fitting tube body 340 coupled to a rear end of the needle assembly 380 and coupled to a needle coupling unit 220 provided at a front end of the handpiece body 200.

The handpiece body 200 is provided with the syringe 100 mounted at an upper portion, and includes a cartridge coupling unit 270 to which the needle cartridge 300 including needles 302 is coupled at a front end. A separate syringe mounting unit 210 may be formed at the upper portion to mount the syringe 100, and the syringe mounting unit 210 may be formed integrally with the handpiece body 200.

The cartridge coupling unit 270, to which the needle cartridge 300 is coupled, is formed at the front end of the handpiece body 200.

The cartridge coupling unit 270 is open on both ends, and includes a passage formed therein, and fitted with the needle cartridge 300.

For a secure fastening of the needle cartridge 300 and the cartridge coupling unit 270, a fixing means may be provided, which may include, in an embodiment, a protrusion 343 formed on the needle cartridge 300, and a corresponding insertion groove 274 formed on the cartridge coupling unit 270. More specifically, the needle cartridge 300 includes a cartridge body 320 to be in contact with the skin, a needle assembly 380 coupled within the cartridge body 320, and a fitting tube body 340 coupled to a rear end of the needle assembly 380 and coupled to the cartridge coupling unit 270 provided at the front end of the handpiece body 200, and a rod 382 whose one side is inserted into the fitting tube body 340 and coupled to the needle assembly 380, and the other side is passed through the cartridge coupling unit 270 and coupled to the needle coupling unit 220.

The fitting tube body 340 includes a mounting end formed on an outer peripheral surface, and the mounting end may be provided with a fixing means for secure coupling with the cartridge coupling unit 270 provided at the front end of the handpiece body 200. An example of the fixing means includes the protrusion 343, although aspects are not limited thereto. That is, the protrusion 343 is provided on the fitting tube body 340 of the needle cartridge 300. There may be a mounting end formed on an outer peripheral surface of the fitting tube body 340, and the protrusion 343 may be formed on the mounting end to be fixed in the handpiece body 200.

In order to correspond to the protrusion 343, the cartridge coupling unit 270 formed at the front end of the handpiece body 200 may include the insertion groove 274 into which the protrusion 343 is inserted. The fitting tube body 340 is fixed to the cartridge coupling unit 270 by fitting the insertion groove 274 and the protrusion 343, and accordingly, the cartridge body 320 and the fitting tube body 340 of the needle cartridge 300 are coupled with the handpiece body 200 fixedly so as not to be moved.

The cartridge coupling unit 270 is open on both ends and includes a passage formed therein, and also includes an insertion guide groove 272 which is in communication with the opening on one end and is formed horizontally in an inner peripheral surface to receive the protrusion 343 to be inserted therein, and an insertion groove 274 which is in communication with the insertion guide groove 272 and is extended through an outer peripheral surface in a direction different from the insertion guide groove 272. Preferably, the insertion groove 274 is formed at a right angle to the insertion guide groove 272. Therefore, when the fitting tube body 340 is inserted into the cartridge coupling unit 270, the protrusion 343 is inserted into the insertion guide groove 272 and then rotated in one direction to be inserted into the insertion groove 274, and the coupling is complete.

The example of the fixing means for securely fastening the needle cartridge 300 and the cartridge coupling unit 270 is described above, but aspects are not limited thereto, and the fixing may be achieved through interference fitting or bonding, and includes all means for fixing the needle cartridge 300 within the handpiece body 200 so that the needle cartridge 300 is not moved. Through this, the cartridge coupling unit 270 is securely fixed to the inner peripheral surface of the handpiece body 200.

In addition, since the cartridge coupling unit 270 is securely fixed in the handpiece body 200, there is an effect that the fitting tube body 340 of the needle cartridge coupled with the cartridge coupling unit 270 is fixed in the handpiece body 200, and the cartridge body 320 coupled to the fitting tube body 340 is also fixed in the handpiece body 200. Through this, the cartridge coupling unit 270 is securely fixed to the inner peripheral surface of the handpiece body 200, and the needle coupling unit 220 is reciprocated stably forward and backward within the handpiece body 200.

The needle coupling unit 220 includes a bar 222 of a predetermined length, a ring part 224 formed at one end of the bar 222 and having a coupling hole coupled to a bearing 430, and a fastening tube body 226 formed at the other end of the bar 222 and having a protrusion coupling hole 227 into which the rod 382 of the needle cartridge 300 is coupled.

A slit 228, into which the end of the rod 382 is inserted, is formed on the front of the fastening tube body 226.

Meanwhile, an O-ring is coupled to an outer surface of the fastening tube body 226, and the O-ring is closely fitted in the handpiece body 200 to absorb vibration.

The syringe pressing unit 600 includes a power source 620 mounted inside the handpiece body 200, a shaft 640 rotatably connected to the power source 620, and a pusher 660 which is screwed to the shaft 640, is inserted into a moving groove 204 formed in a longitudinal direction in an upper portion of the handpiece body 200, and is moved to push the plunger 140 of the syringe 100.

The power source 620 is a second motor with an axis disposed horizontally. The shaft 640 is connected to the axis of the second motor and arranged horizontally, and a body 662 formed on a lower portion of the pusher 660 is screwed to the shaft 640.

As the second motor is driven, the axis and the shaft 640 are rotated in one direction or the other direction, thus driving the pusher 660 forward or backward. The pusher 660 driven forward may push the plunger 140 of the syringe so that the chemical solution may be discharged.

As the second motor is driven, the axis and the shaft 640 are rotated in one direction so that the pusher 660 is driven forward, and the pusher 660 pushes the plunger 140 of the syringe 100 to discharge the chemical solution, such that the chemical solution flows into an injection port 310 of the needle cartridge 300 through the injection needle 182, and the chemical solution fills a space L defined when the cartridge body 320 is in contact with the skin. When the chemical solution in the syringe 100 is used up during the procedure, the second motor is driven and the axis and the shaft 640 are rotated in the other direction to drive the pusher 660 backward, and when the pusher 660 is moved backward and separated from the plunger 140 of the syringe 100, the syringe 100 is removed and replaced with the syringe 100 filled with the chemical solution and the procedure may continue.

The needle driving unit 400 is mounted inside the handpiece body 200 and linearly drives the needle coupling unit 220 in the forward and backward directions such that the needle 302 of the needle cartridge 300 is continuously raised and lowered.

The needle driving unit 400 includes a first motor 410 disposed with an axis 411 facing upward, a motor mounting case 420 on which the first motor 410 is mounted and an opening is formed on one side, the bearing 430 inserted into the motor mounting case 420 and eccentrically coupled with the axis 411, and a cap 440 coupled to an upper end of the axis 411.

The ring part 224 of the needle coupling unit 220 is inserted into the opening of the motor mounting case 420 and fitted into the bearing 430. Therefore, when the first motor 410 is turned on, the axis 411 is rotated, the bearing 430 connected to the axis 411 is rotated eccentrically, and the bar 222 coupled to the bearing 430 is restricted to the opening of the motor mounting case 420 such that the eccentric rotational movement is converted into a linear motion of the bar 222, so that the needle assembly 380 is moved forward and backward, thereby performing repeatedly the operation of contacting or separating the needle 302 with respect to the skin.

Since the cartridge coupling unit 270 is securely fixed to the handpiece body 200, there is an effect that the fitting tube body 340 of the needle cartridge coupled with the cartridge coupling unit 270 and the cartridge body 320 coupled to the fitting tube body 340 are also fixed to the handpiece body 200. Through this, the cartridge coupling unit 270 is securely fixed to the inner peripheral surface of the handpiece body 200, and the needle assembly 380 is coupled to the needle driving unit 400, such that the needle coupling unit 220 is reciprocated stably forward and backward within the handpiece body 200 by the operation of the needle driving unit 400.

Meanwhile, the position control unit 500 may be further included, which moves the needle driving unit 400 forward and backward to adjust its position, thereby adjusting the length by which the needle 302 is pulled out.

The position control unit 500 includes an operating axis 520 including a screw thread 523 formed on a portion thereof, in which one end of the operating axis 520 is fitted into the mounting unit 490 formed on the motor mounting case 420 of the needle driving unit 400, and a handle 560 coupled to the other end of the operating axis 520 and formed outside of the handpiece body 200.

As shown in FIG. 4, by manually turning the handle 560 of the position control unit 500, it is possible to move the needle driving unit 400 forward or backward and adjust the position. By adjusting the position of the needle driving unit 400 in this way, it is possible to adjust the length by which the needles 302 of the needle assembly 380 connected thereto can be pulled out, thereby adjusting the depth of insertion into the skin.

As shown in FIGS. 5 to 8, the needle cartridge 300 includes the cartridge body 320 to be in contact with the skin, the needle assembly 380 coupled within the cartridge body 320, and the fitting tube body 340 coupled to the rear end of the needle assembly 380 and coupled to the needle coupling unit 220 provided at the front end of the handpiece body 200.

In addition, the needle cartridge 300 may include the rod 382 whose one side is inserted into the fitting tube body 340 and coupled to the needle assembly 380, and the other side is coupled with the needle driving unit 400.

The needle driving unit 400 is connected to a fastening tube body 226 having a coupling hole into which the rod 382 is coupled, and the fastening tube is connected to the motor and driven in forward and backward directions so as to move needles 381 into contact with the skin or separate the needles 381 from the contact with the skin repeatedly.

The cartridge body 320 includes an opening 326 formed at one end in contact with the skin, and a connection end 322 formed at the other end to which the fitting tube body 340 is coupled.

A protrusion 324 connected to a partition wall 330 is formed on a portion of the connection end 322, and an extension part 325, raised in an arc shape, is formed above the protrusion 324.

The extension part 325 is connected in communication with an injection port 310 to be described below, and the protrusion 324 is located under the injection port 310 to be described below so as to guide the injection needle 182 of the syringe 100 to contact the protrusion 324 and then slide and bend toward an upper surface of the partition wall 330.

The partition wall 330 connected to the injection port 310 is formed in the cartridge body 320, and a flow path 350 is formed between the partition wall 330 and the inner peripheral surface. The injection needle 182 of the syringe 100 is partially inserted into the flow path 350, and the chemical solution may flow into the flow path 350 through the injection needle 182.

Preferably, an end of the partition wall 330 is spaced apart from the opening 326 so that the introduced chemical solution can be discharged from the end of the partition wall 330 and fill the space defined between the end of the partition wall 330 and the end to the opening 326.

The fitting tube body 340 includes an opening 342 formed on one side into which the connection end 322 is fitted, the injection port 310 formed on an outer peripheral surface, into which the injection needle 182 of the syringe 100 is inserted, and a mounting end 344 formed on an outer peripheral surface, which is fitted into the needle coupling unit 220 provided at the front end of the handpiece body 200 provided on the other side.

The needle assembly 380 is coupled within the cartridge body 320 and the fitting tube body 340 which are connected to each other, and the needle assembly 380 is connected to the rod 382.

Meanwhile, the protrusion 343 may be formed on an outer peripheral surface of the mounting end 344. The protrusion 343 is coupled within the cartridge coupling unit 270 provided at the front end of the handpiece body 200.

The cartridge coupling unit 270 includes the insertion groove 272 into which the protrusion 343 is inserted, and the protrusion coupling hole 274 which is formed in communication with the insertion groove 272, is extended through the outer peripheral surface of the handpiece body 200, and is formed at a right angle with respect to the insertion groove 272. Therefore, when the fitting tube body 340 is inserted into the cartridge coupling unit 270, the protrusion 343 is inserted into the insertion groove 272 and then rotated in one direction to be inserted into the protrusion insertion groove 274, and the coupling is complete.

The needle assembly 380 includes one or more needles 381. More specifically, the needle assembly 380 is inserted into the cartridge body 320 and includes a plurality of needles 381 formed on one side, and a needle fixing unit 384 including a rod coupling unit 383 formed on the other side, to which the rod 382 is coupled.

The rod 382 includes a hook 386 formed at one end and coupled to the rod coupling unit 383, a locking end 387 formed at the other end and coupled to the coupling unit 270 of the handpiece body 200. A spring 385 is disposed around an outer surface of the rod 382.

The impact generated when the needles 381 come into contact with the skin can be absorbed by the spring 385.

The needle 381 has a fine size, so it causes little pain when inserted into the body and is minimally invasive. The needle 381 has a needle shape with a pointed end and is disposed on an upper portion of the needle fixing unit 384. By the "pointed end", it means a part including a pointed end (tip), and the pointed end may have a sharpness sufficient to penetrate the stratum corneum of the skin when the needle is applied to the skin. The needle fixing unit 384 may have a cylindrical or truncated cone shape and may refer to a portion that is integrally connected to the pointed end to form a body of the needle. For example, the needle may have a shape like a bullet, but aspects are not limited thereto.

An end of the partition wall 330 is spaced apart from the end of the cartridge body 320 to form a space L near the opening 326. Since the chemical solution is collected in the space (L) and confined near the opening 326, when needles are passed through this space to be penetrated into the skin, the needles are applied with the chemical solution thereon and penetrated into the skin so that the chemical solution penetrates into the punctures created in the skin.

When coupled, the cartridge body 320 and fitting tube body 340 are connected and fixed to the handpiece body 200 by the needle coupling unit 220, and the needle assembly 380 is connected and fixed to the needle driving unit 400. While the needle assembly 380 is moved forward and backward by the operation of the needle driving unit 400 provided in the handpiece body 200, the cartridge body 320 and the fitting tube body 340 are fixedly connected to the handpiece body, and accordingly, during the treatment, the cartridge body 320 is brought into contact with the skin, and the needle assembly 380 is moved forward and backward such that, after the chemical solution filled in the space L is applied on the surface of the needle 381, the needles 381 penetrate the skin to form punctures, and the chemical solution applied on the needles 381 is injected into the punctures in the skin. After the needles 381 are moved backwards and removed from the skin, the chemical solution remains in the skin and the punctures formed in the skin are recovered by the skin's self-regenerative power and the chemical solution is trapped in the skin. If the chemical solution contains ink or pigment, the ink and pigment remain in the skin, making tattooing possible.

The needle cartridge configured as described above is coupled to the needle coupling unit 220 provided at the front end of the handpiece body 200, as shown in FIGS. 1 to 4.

The needle coupling unit 220 includes the bar 222 having a predetermined length, the ring part 224 formed at one end of the bar 222 and having the coupling hole coupled to the bearing 430, and the fastening tube body 226 formed at the other end of the bar 222 and having the protrusion coupling hole 227 into which the rod 382 of the needle cartridge 300 is coupled. The position control unit 500 includes the operating axis 520 including the screw thread 523 formed on a portion thereof, in which one end of the operating axis 520 is fitted into the mounting unit 490 formed on the motor mounting case 420 of the needle driving unit 400, and the handle 560 coupled to the other end of the operating axis 520 and formed outside of the handpiece body 200. The fitting tube body is coupled with the handpiece body and fixedly coupled so as not to be moved. The needle assembly is coupled to the needle driving unit and reciprocated forward and backward by the operation of the needle driving unit. The position control unit adjusts the handle so as to move the position of the needle driving unit in the handpiece body, thereby adjusting the moving distance of the needles of the needle assembly that are pulled out of the needle cartridge body and controlling the depth by which the needles are inserted into the skin.

According to one example, the needles 302 may be set to protrude out of the cartridge body 320 by about 2 mm at the maximum when the needle assembly 380 is moved by a distance of about 2 mm by the operation of the first motor 410. Therefore, the depth by which the needles 302 are inserted into the skin is about 2 mm. If it is desired to change the insertion depth of the needles 302 into the skin to 1.5 mm, the needles 302 should be protruded 1.5 mm out of the cartridge body 320. To this end, the handle 560 of the position control unit 500 is turned so that the needle driving unit 400 is moved backward to the rear of the handpiece body 200 by 0.5 mm. Since the fitting tube body 340 and the cartridge body 320 of the needle cartridge 300 are coupled with the handpiece body 200 and fixed so as not to be moved, the needle assembly 380, which is relatively movable, is coupled to the needle driving unit 400 and reciprocated forward and backward according to the operation of the needle driving unit 400, and the needle driving unit 400 is moved backward to the rear of the handpiece body 200 by 0.5 mm. Accordingly, even when the needle assembly 380 is moved by the distance of 2 mm, the needles 302 may protrude 1.5 mm outside the cartridge body 320, and the depth of the needles 302 inserted into the skin may be adjusted to 1.5 mm. As described above, the length of the needles exposed can be changed by adjusting the position control unit, thereby adjusting the depth to conduct the treatment.

For the position control unit 500, the handle 560 is described as an example that moves the position of the needle driving unit 400 in the handpiece body 200 to adjust the length of the needles 302 pulled out of the needle cartridge 300. However, it should be understood that the aspects are not limited to the handle 560, and any means for adjusting the position of the needle driving unit 400 may be included.

Meanwhile, in order to stably assist the coupling of the position control unit 500 and the motor mounting case 420, the position control unit 500 may further include a fixing member 540 that is screwed to the operating axis 520 and coupled with the interior of the handpiece body 200. Since the fixing member 540 is fixed to the handpiece body 200, it is possible to prevent a movement of the operating axis 520 that may occur not by the manipulation of the handle 560, but by the vibration of the first motor 410.

More preferably, a ring plate 522 may be formed at one end of the operating axis 520, which may be inserted into the mounting unit 490 and which may have a larger diameter than a fitting unit 492.

The mounting part 490 formed on the motor mounting case 420 includes the fitting part 492 into which the operating axis 520 is inserted, and prevents the operating axis 520 from being separated from the mounting portion 490 in the process of rotating.

A guiding means for guiding the forward and backward movement of the motor mounting case 420 may also be included.

The guide means includes a guide piece 422 protruding from a side of the motor mounting case 420, and a guide rail unit 426 formed on the inner peripheral surface of the handpiece body 200 to be coupled with the guide piece 422. The guide means stably fastens a first motor 400 to the handpiece body 200, and also distributes vibration caused by the operation of the first motor 400 to the handpiece body 200.

The injection needle 182 of the syringe is first inserted into the injection port 310 and then mounted on the syringe mounting part 210, and the injection needle may be bent because the injection needle 182 is inserted into the injection port 310 located relatively below the syringe device unit 210. The chemical solution is injected through the injection needle 182 and flows into the space L through the flow path 350 such that the chemical solution is collected in the space L and confined near the opening 326.

The syringe pressing unit 600 is turned on and the chemical solution is injected into the cartridge body 320. Therefore, the chemical solution injected through the injection port 310 with the cartridge body 320 in close contact with the skin, is injected through the flow path 350 and then collected and confined near the opening 326 of the cartridge body 320, so that the needles 381 passing through the chemical solution is applied with the chemical solution thereon before being inserted into the skin, and as a result, the chemical solution can be injected into the skin at the same time as the needles 381 are inserted.

According to the needle cartridge for drug injection and the drug injection device including the same, the needles are applied, on the surfaces thereof, with chemical solution including drug, pigments, and ink filled in the needle cartridge and then inserted into the skin so that it is possible to inject the chemical solution into the skin concurrently as the needles applied with the chemical solution pierce the skin leaving punctures, such that the injection efficiency of the chemical solution can be improved, and the length by which the needles are pulled out can be finely adjusted, thereby improving the accuracy of the procedure.

Although the description has been made in relation to certain embodiments, it will be readily apparent to those skilled in the art that various modifications and variations can be made without departing from the gist and scope of the disclosure, and it is obvious that all such changes and modifications fall within the scope of the appended claims.

The invention claimed is:

1. A needle cartridge for drug injection and a drug injecting device including the same, comprising:
the needle cartridge comprising a needle;
a handpiece body including a syringe formed on an upper portion, and a cartridge coupling unit and a needle coupling unit formed on a front;
a syringe pressing unit including a power source mounted inside the handpiece body, a shaft connected to the power source and rotated, and a pusher which is coupled to the shaft, is inserted into a moving groove formed in a longitudinal direction in the upper portion of the handpiece body, and is moved to push a plunger of the syringe;
a needle driving unit mounted inside the handpiece body and reciprocating the needle of the needle cartridge in forward and backward directions; and
a position control unit that moves a position of the needle driving unit in the handpiece body to adjust a length of the needle pulled out of the needle cartridge,
wherein the needle cartridge comprises:
a cartridge body to be in contact with skin;
a fitting tube body coupled to a rear end of the cartridge body, and including an injection port formed on an outer peripheral surface, an opening, formed on one side, for fitting with a connection end, a mounting end formed on the outer peripheral surface on other side, and a protrusion formed on the mounting end;
a needle assembly including a rod to be inserted into the fitting tube body and coupled with the needle driving unit; and
the connection end formed at other end and coupled with the fitting tube body, the needle coupling unit comprises:
a bar having a predetermined length;
a ring part formed at one end of the bar and having a coupling hole coupled with a bearing; and
a fastening tube body formed at the other end of the bar and having a protrusion coupling hole into which the rod of the needle cartridge is coupled, the needle assembly includes
the rod to be inserted into the fitting tube body and coupled with the needle driving unit,
the cartridge coupling unit is open on both ends, and includes a passage formed therein, and an insertion groove formed on an outer peripheral surface, and
the protrusion of the mounting end and the insertion groove of the cartridge coupling unit are fitted with each other.

2. The needle cartridge and the drug injecting device of claim 1, wherein
the cartridge body includes:
an opening formed at one end to be in contact with the skin; and
a partition wall formed within the cartridge body and connected to the injection port, and
a flow path is formed between the partition wall and an inner peripheral surface of the cartridge body,
the mounting end is coupled with the handpiece body and fixed so as not to be moved, and
the partition wall is formed such that an end is spaced apart from the opening, defining a space therebetween, and when the cartridge body is brought into contact with the skin, the space is filled with a chemical solution.

3. The needle cartridge and the drug injecting device of claim 1, wherein
the needle driving unit includes:
a first motor disposed with an axis facing upward;
a motor mounting case to which the axis is coupled, on which the first motor is mounted, and which is connected to the needle coupling unit;
the bearing inserted into the motor mounting case and eccentrically coupled with the axis; and
a cap coupled to an upper end of the axis.

4. The needle cartridge and the drug injecting device of claim 1, comprising a guiding means for guiding forward and backward movement of the motor mounting case, wherein
the guiding means includes:
a guide piece protruding from a side of a motor mounting case; and
a guide rail unit formed on an inner peripheral surface of the handpiece body and coupled with the guide piece,
the motor mounting case includes an opening formed on one side.

5. The needle cartridge and the drug injecting device of claim 1, wherein
the power source is a second motor with an axis disposed horizontally, wherein the shaft is connected to the axis of the second motor and disposed horizontally, and a body formed at a lower portion of the pusher is coupled to the shaft.

6. The needle cartridge and the drug injecting device of claim 1, wherein the position control unit includes:

an operating axis coupled to a motor mounting case of the needle driving unit and including threads formed on a portion thereof; and a handle coupled to other end of the operating axis and formed outside of the handpiece body.

\* \* \* \* \*